(12) United States Patent
Nukui et al.

(10) Patent No.: US 6,466,639 B2
(45) Date of Patent: Oct. 15, 2002

(54) X-RAY CT IMAGING METHOD, SUBJECT CENTER POSITION DETECTION METHOD, AND X-RAY CT APPARATUS

(75) Inventors: Masatake Nukui, Tokyo (JP); Akihiko Nishide, Tokyo (JP)

(73) Assignee: GE Yokogawa Medical Systems, Limited, Tokyo (JP)

(*) Notice: Subject to any disclaimer, the term of this patent is extended or adjusted under 35 U.S.C. 154(b) by 15 days.

(21) Appl. No.: 09/751,953

(22) Filed: Dec. 29, 2000

(65) Prior Publication Data

US 2001/0007585 A1 Jul. 12, 2001

(30) Foreign Application Priority Data

Jan. 7, 2000 (JP) ........................................ 2000-001484

(51) Int. Cl.$^7$ ................................................. A61B 6/03
(52) U.S. Cl. ............................................. 378/8; 378/20
(58) Field of Search .......................... 378/4, 8, 20, 95, 378/205

(56) References Cited

U.S. PATENT DOCUMENTS 3,983,715 A   10/1976  Hair
5,457,724 A * 10/1995  Toth ............................... 378/4
6,269,501 B1 * 8/2001  Li et al. .......................... 5/601

FOREIGN PATENT DOCUMENTS

| DE | 3528821 | 12/1987 |
|----|---------|---------|
| JP | 06118030 | 4/1994 |
| JP | 10099319 | 4/1998 |
| JP | 11188030 | 7/1999 |

* cited by examiner

Primary Examiner—David P. Porta
Assistant Examiner—Therese Barber
(74) Attorney, Agent, or Firm—Moonray Kojima

(57) ABSTRACT

In order to detect whether the center position of a subject is offset from a scan center and notify a human operator of the result of the detection, the subject center position is detected based on a projection profile of a parallel view at a view angle of 90° (S5). If the distance between the subject center position and the scan center exceeds a predefined range (e.g., 50 cm) (S6), a warning is displayed on a CRT to prompt the operator to adjust the position of the subject and repeat imaging (S7).

8 Claims, 4 Drawing Sheets

X-RAY CT IMAGING METHOD, SUBJECT CENTER POSITION DETECTION METHOD, AND X-RAY CT APPARATUS

BACKGROUND OF THE INVENTION

The present invention relates to an X-ray CT (Computed Tomography) imaging method, subject center position detection method and X-ray CT apparatus, and more particularly to an X-ray CT imaging method, subject center position detection method and X-ray CT apparatus which can detect whether the center position of a subject is significantly offset from a scan center.

In X-ray CT imaging, a human operator adjusts the height of a top plate for laying a subject by visual measurement so that the center position of the subject coincides with a scan center (a center of rotation of an X-ray tube) with minimum offset.

However, the adjustment by the operator's visual measurement sometimes makes the center position of the subject significantly offset from the scan center, which results in poor homogeneity in the CT value of a subject's image. Moreover, overrange may occur near the scan center, when the scan center falls outside the subject.

SUMMARY OF THE INVENTION

It is therefore an object of the present invention to provide an X-ray CT imaging method, subject center position detection method and X-ray CT apparatus which can detect whether the center position of a subject is significantly offset from a scan center.

In accordance with a first aspect of the present invention, there is provided an X-ray CT imaging method for performing a scan by an X-ray tube rotating around a subject, comprising the steps of: detecting a subject center position based on a projection profile acquired by imaging the subject; and giving a warning when a calculated distance between the subject center position and a scan center exceeds a predefined range.

The X-ray CT imaging method of the first aspect displays a warning on a display screen or gives a vocal prompt to a human operator to adjust the position when the subject center position is offset from the scan center by an amount exceeding a predefined range (e.g., 50 cm). Thus, the method can detect whether the center position of a subject is significantly offset from a scan center.

In accordance with a second aspect, there is provided a subject center position detection method comprising the steps of: acquiring a projection profile by imaging a subject from a direction orthogonal to a plane containing a body axis of the subject by an X-ray CT apparatus for performing a scan by an X-ray tube rotating around the subject; defining an X-ray detector channel index corresponding to a calculated centroid of the projection profile as a centroid channel index; examining a projection value in the projection profile toward a direction along a first direction of the subject from the centroid channel index; defining a channel index having a projection value no more than a predetermined projection value threshold $P_{th}$ as a first threshold channel index; examining on the other hand a projection value in the projection profile toward a direction along a second direction of the subject opposite to the first direction from the centroid channel index; defining a channel index having a projection value no more than the predetermined projection value threshold $P_{th}$ as a second threshold channel index; defining an intermediate value between the first and second threshold channel indices as a subject position channel index; and obtaining a subject center position from the subject position channel index.

A projection profile acquired by imaging a subject lying on a top plate from a direction orthogonal to a plane containing the subject's body axis contains a projection of the top plate as well as a projection of the subject. Thus, the centroid of the projection profile is shifted toward the top plate relative to a subject center position. Therefore, the subject center position should be determined on a side opposite to the top plate with respect to the centroid of the projection profile.

The subject center position detection method of the second aspect introduces "projection value threshold $P_{th}$," as a parameter, searches channels having respective values no more than the projection value threshold $P_{th}$ in two directions, calculates an intermediate of the retrieved two channels, and determines the subject center position on a side opposite to the top plate with respect to the centroid of the projection profile based on the intermediate. Thus, the subject center position can be accurately determined with the effect of the top plate eliminated.

In the subject center position detection method of the above configuration, the projection value threshold $P_{th}$ may be selected empirically as, for example, ½ of a projection value corresponding to the centroid channel index.

Moreover, in the subject center position detection method of the above configuration, the subject center position can be determined more accurately by first removing profiles other than the subject's profile from the projection profile, and then calculating the centroid.

In accordance with a fifth aspect, there is provided an X-ray CT apparatus for performing a scan by an X-ray tube rotating around a subject, comprising: projection profile acquisition means for acquiring a projection profile by imaging the subject; subject position detection means for detecting a subject center position based on the acquired projection profile; and warning displaying means for displaying a warning when the distance between the subject center position and a scan center exceeds a predefined range.

The X-ray CT apparatus of the fifth aspect can suitably implement the X-ray CT imaging method as described regarding the first aspect.

In accordance with a sixth aspect, there is provided an X-ray CT apparatus for performing a scan by an X-ray tube rotating around a subject, comprising subject center position detection means configured to: define an X-ray detector channel index corresponding to a calculated centroid of a projection profile acquired by imaging a subject from a direction orthogonal to a plane containing a body axis of the subject as a centroid channel index; examine a projection value in the projection profile toward a direction along a first direction of the subject from the centroid channel index; define a channel index having a projection value no more than a predetermined projection value threshold $P_{th}$ as a first threshold channel index; examine on the other hand a projection value in the projection profile toward a direction along a second direction of the subject opposite to the first direction from the centroid channel index; define a channel index having a projection value no more than the predetermined projection value threshold $P_{th}$ as a second threshold channel index; define an intermediate value between the first and second threshold channel indices as a subject position channel index; and obtain a subject center position from the subject position channel index.

The X-ray CT apparatus of the sixth aspect can suitably implement the subject center position detection method as described regarding the second aspect.

In the X-ray CT apparatus of the above configuration, the projection value threshold $P_{th}$ may be selected empirically as, for example, ½ of a projection value corresponding to the centroid channel index.

Moreover, in the X-ray CT apparatus of the above configuration, the subject center position can be determined more accurately by first removing profiles other than the subject's profile from the projection profile, and then calculating the centroid.

To remove profiles other than the subject's profile from the projection profile, a one-dimensional minimum value filter, followed by a one-dimensional maximum value filter, for example, may be applied to the projection file.

The X-ray CT imaging method, subject center position detection method and X-ray CT apparatus of the present invention can detect whether the center position of a subject is offset from a scan center, and can notify an operator of the result of the detection. Thus, even when the subject center position is significantly offset from the scan center, the position of the subject is adjusted and imaging is repeated, whereby an X-ray image with good quality can be obtained.

Further objects and advantages of the present invention will be apparent from the following description of the preferred embodiments of the invention as illustrated in the accompanying drawings.

DETAILED DESCRIPTION OF THE INVENTION

Figure 1A:
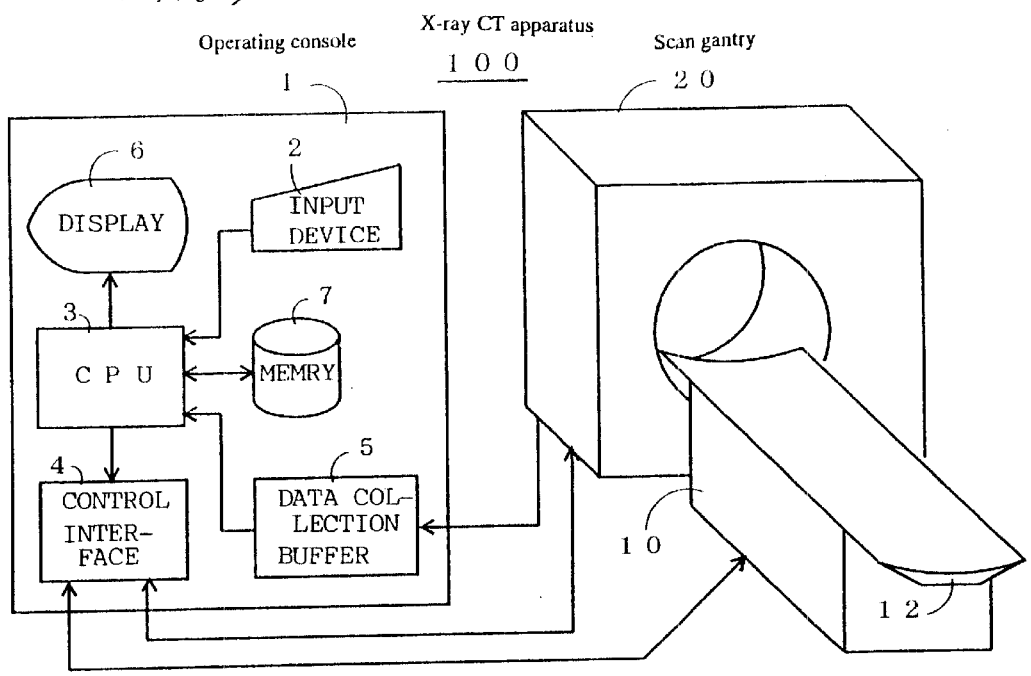
FIG. 1 is a block diagram illustrating the configuration of an X-ray CT apparatus in accordance with a first embodiment of the present invention.
Figure 1B:
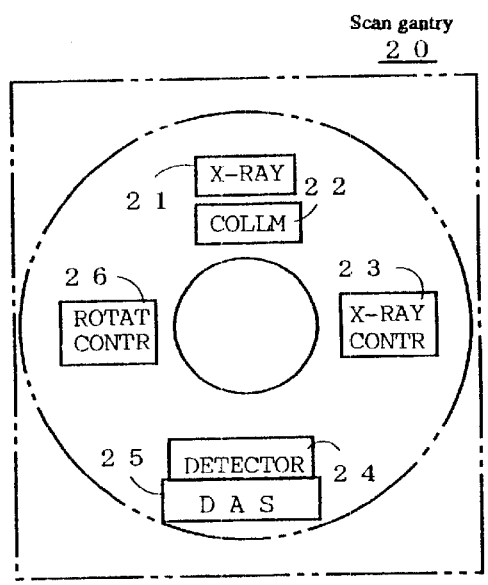

The present invention will now be described in more detail with reference to embodiments shown in the accompanying drawings.
-First Embodiment-
FIG. 1 is a block diagram illustrating the configuration of an X-ray CT apparatus in accordance with a first embodiment of the present invention.

The X-ray CT apparatus 100 comprises an operating console 1, a table apparatus 10 and a scan gantry 20.

The operating console 1 comprises an input device 2 for accepting instructions and information from a human operator, a central processing apparatus 3 for executing a scan process, an image reconstruction process and a subject center position detection process of the present invention, a control interface 4 for transmitting/receiving control signals and the like to/from the table apparatus 10 and the scan gantry 20, a data collection buffer 5 for collecting data acquired at the scan gantry 20, a CRT 6 for displaying an X-ray image and a warning, and a storage device 7 for storing programs and data.

The table apparatus 10 comprises a height-variable top plate 12 for carrying a subject into/out of a bore in the scan gantry 20. The top plate 12 is driven by a motor incorporated in the table apparatus 10.

The scan gantry 20 comprises an X-ray tube 21, a collimator 22, an X-ray controller 23, a detector 24, a DAS (data acquisition system) 25, and a rotation controller 26 for rotating the X-ray tube 21 and other associated components around the subject.

Figure 2:
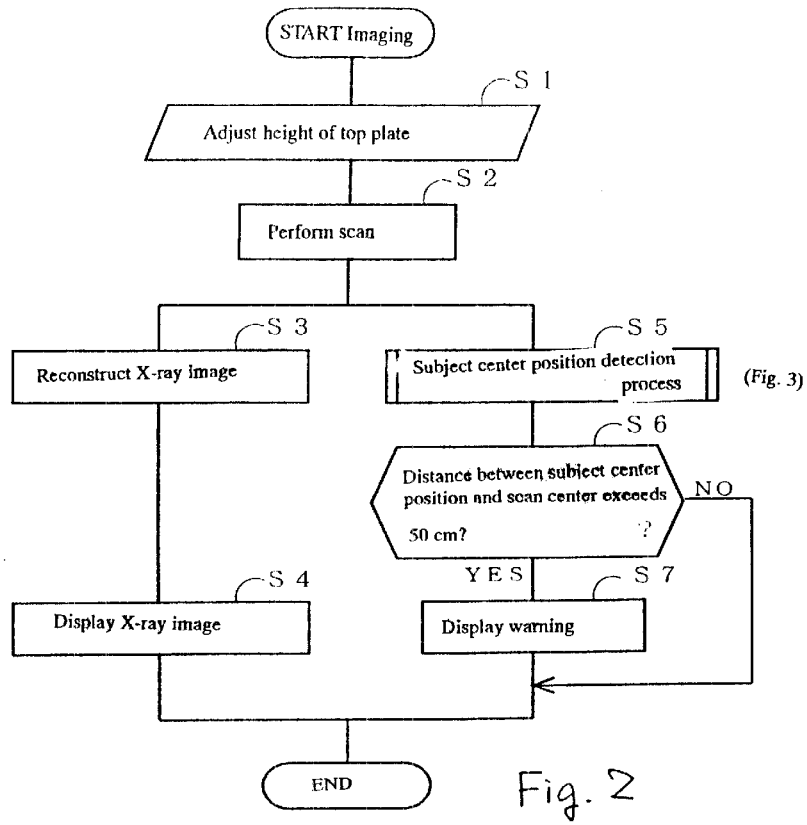
FIG. 2 is a flow chart illustrating an X-ray CT imaging procedure in accordance with the first embodiment.

FIG. 2 is a flow chart illustrating an X-ray CT imaging procedure in accordance with this embodiment.

In Step S1, an operator adjusts the height of the top plate 12 by visual measurement so that the subject center position coincides with the center of the bore.

In Step S2, a scan is performed while rotating the X-ray tube 21, detector 24 and other associated components around the subject. Then, Steps S3, S4 and Steps S5, S6, S7 are executed in parallel.

In Step S3, an X-ray image is reconstructed from data collected by the scan.

In Step S4, the X-ray image is displayed on the CRT 6.

In Step S5, the subject center position is determined by a subject center position detection process (which will be described later with reference to FIG. 3).

In Step S6, the distance Δ between the determined subject center position and the scan center is calculated, and if the distance Δ exceeds a predefined range, for example, up to 50 cm, the process goes to Step S7; otherwise the process is terminated.

In Step S7, since the subject center position is significantly offset from the scan center, a warning message is displayed on the CRT 6 to tell the operator to move the top plate 12 by Δ cm either in a first direction or in a second direction opposite to the first direction, more particularly, in an upper direction or in a lower direction of the height of the top plate 12.

According to the above imaging process, since a warning is given when the subject center position is significantly offset from the scan center, imaging can be repeated after adjusting the position, whereby an X-ray image with good quality can be obtained.

Figure 3:
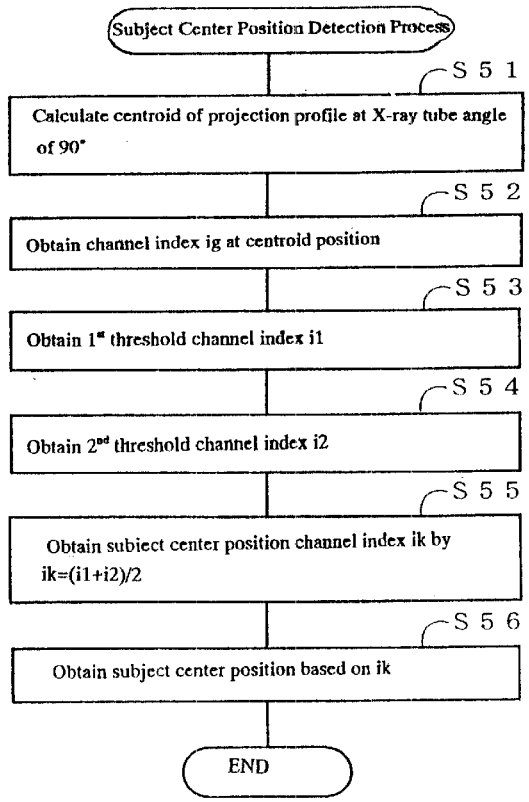
FIG. 3 is a flow chart of a subject center position detection process.

FIG. 3 is a flow chart illustrating the subject center position detection process (Step S5).

In Step S51, a centroid G is calculated in a projection profile of a parallel view at a view angle of 90° which is a direction orthogonal to a plane containing the body axis of the subject Hk.

Figure 4:
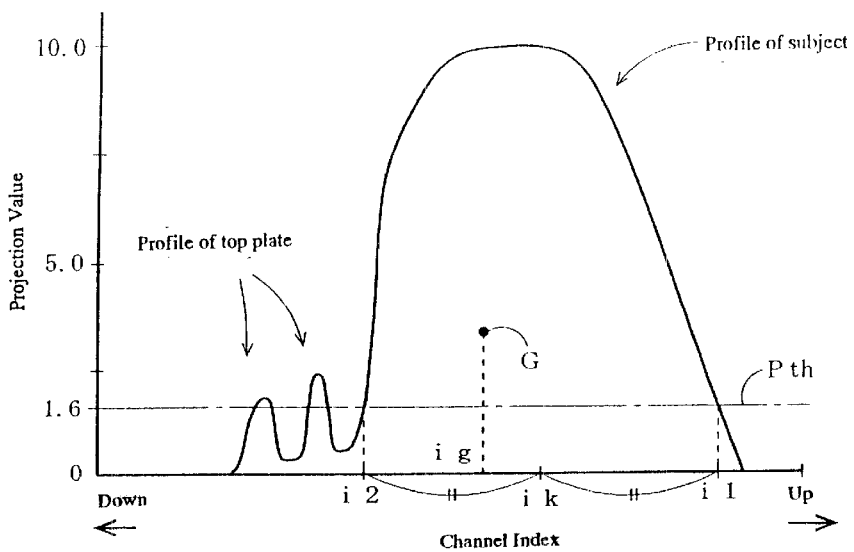
FIG. 4 is a schematic diagram illustrating a projection profile of a parallel view at a view angle of 90°.

The projection profile of a parallel view at a view angle of 90° is exemplarily shown in FIG. 4.

Figure 5:
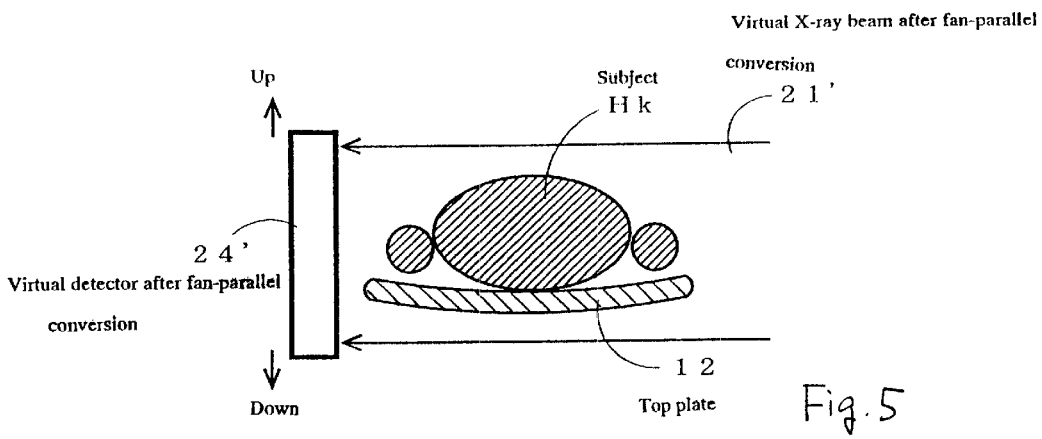
FIG. 5 virtually illustrates the concept of acquisition of the projection profile of a parallel view at a view angle of 90°.

The projection profile is equivalent to one obtained by imaging the subject Hk by casting a parallel X-ray beam 21' to a virtual detector 24' through the subject Hk from an exact lateral side, as shown in FIG. 5, wherein the abscissa of the graph represents the channel index, and the ordinate represents the projection value. The designation "Up" in the drawing represents the upper side of the subject Hk (namely, the side opposite to the top plate 12), or a first direction of the subject Hk. The designation "Down" represents the lower side of the subject Hk (namely, the side of the top plate 12), or a second direction of the subject Hk.

The large swell in the center of the graph represents a profile of the subject and has a peak value of about 10 μx. Two small crests at the left of the graph represent a profile of the top plate 12 detected by the channels at the lower portion, and have peak values of about 1.6–2.0 μx.

It should be noted that a method of obtaining a projection profile of a parallel view from data obtained by a fan-beam scan is disclosed in, for example, Japanese Patent Application Laid Open No. H10-99319.

In Step S52, a channel index corresponding to the centroid G is obtained, and the channel index is defined as a centroid channel index ig.

In Step S53, the projection value in the projection profile is examined from the centroid channel index ig toward the first direction of the subject, i.e., toward the "Up" direction in FIG. 5, or toward the side opposite to the top plate relative to the subject, in other words, in the upper direction of the subject; and a channel index having a projection value no more than a predetermined projection value threshold $P_{th}$ (=1.6 in this example) is defined as a first threshold channel index i1.

In Step S54, the projection value in the projection profile is examined from the centroid channel index ig toward the second direction of the subject opposite to the first direction, i.e., toward the "Down" direction in FIG. 5, or toward the side of the top plate, in other words, in the lower direction of the subject; and a channel index having a projection value no more than the predetermined projection value threshold $P_{th}$ is defined as a second threshold channel index i2.

In Step S55, an intermediate value between the first and second threshold channel index i1 and i2 is defined as a subject center position channel index ik.

In Step S56, the height corresponding to the subject center position channel index ik is calculated, and the calculated height is defined as the subject center position.

According to the above process, the subject center position can be accurately detected with the effect of the top plate 12 eliminated.

-Other Embodiments-

While the projection value threshold $P_{th}$=1.6 in the first embodiment, the projection value threshold may have a different value. For example, the projection value threshold $P_{th}$ may be ½ of the projection value at the centroid channel index ig. In this case, $P_{th}$=5.0 in the example shown in FIG. 4.

Further, while a warning is given when the subject center position is offset from the scan center by more than 50 cm in the first embodiment, the distance may be varied according to the imaged site of the subject.

Figure 6:
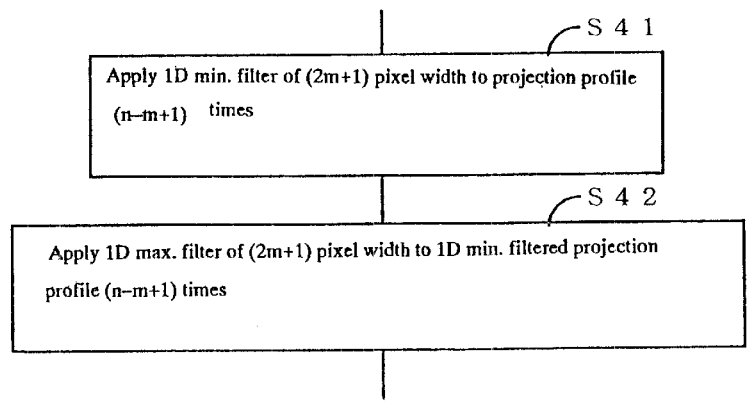
FIG. 6 is a flow chart illustrating a process for removing profiles other than a subject's profile from the projection profile.

Moreover, Steps S41 and S42 shown in FIG. 6 (a process for removing profiles other than the subject's profile from the projection profile) may be inserted before Step S5 in FIG. 2.

Figure 7:
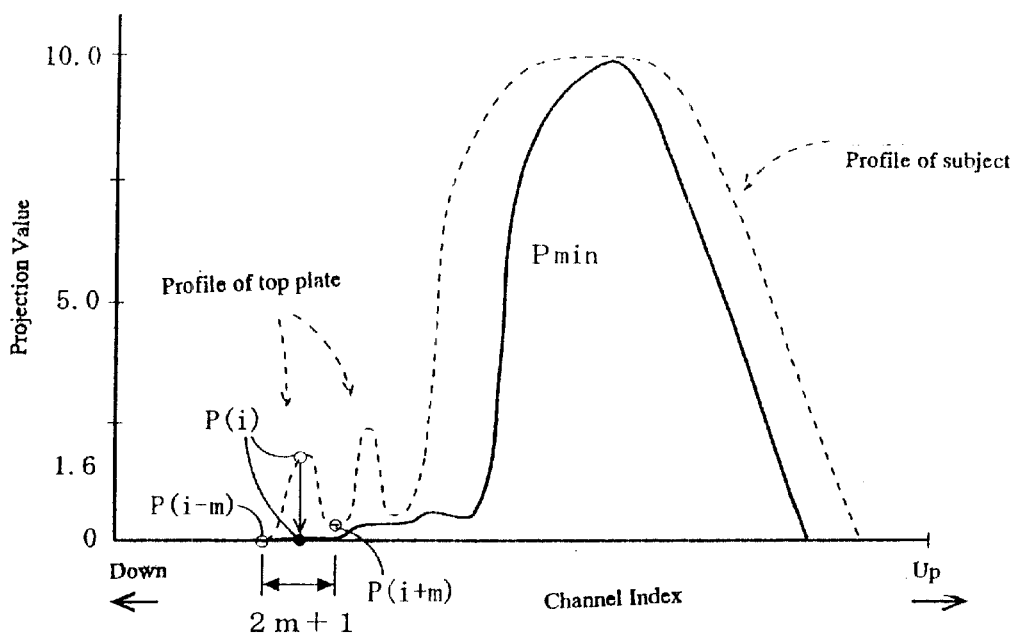
FIG. 7 illustrates the concept of a projection profile after a one-dimensional minimum value filter is applied.

Specifically, in Step S41, a one-dimensional minimum value filter having a pixel width of (2 m+1) is applied (n−m+1) times to the projection profile of a parallel view at a view angle of 90° which is a direction orthogonal to a plane containing the body axis of the subject. More specifically, when the projection value of an i-th channel in the projection profile is represented as P(i), a process in which the minimum value of P(i−m)—P(i+m) is set in P(i) is repeated (n−m+1) times, wherein m and n are integers, and for example, m=1 and n=1. A projection profile $P_{min}$ after the one-dimensional minimum value filter is applied is exemplarily shown in FIG. 7.

Figure 8:
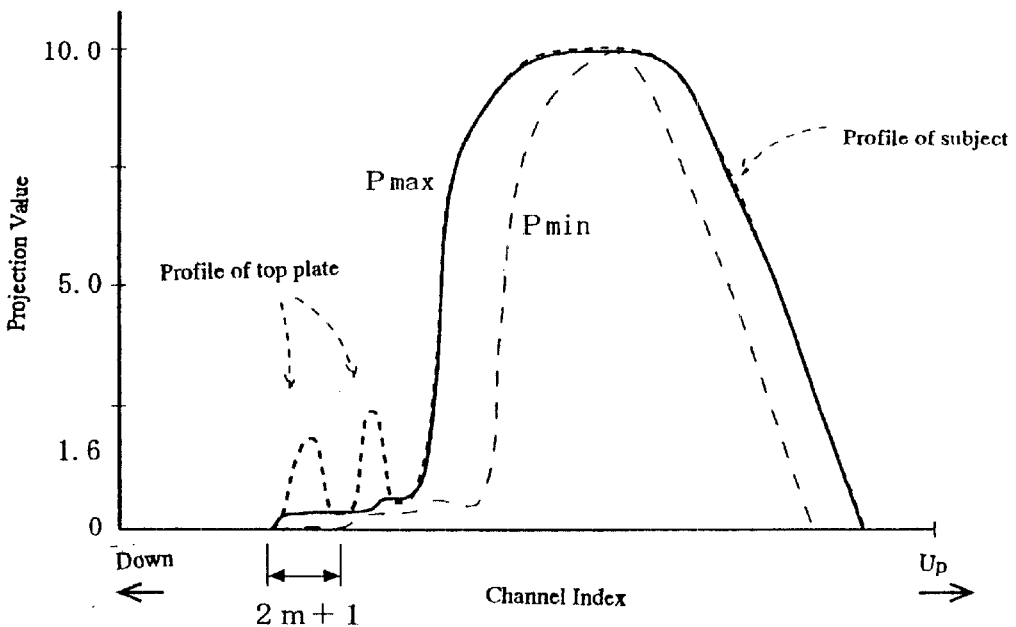
FIG. 8 illustrates the concept of the one-dimensional minimum value filtered projection profile after a one-dimensional maximum value filter is further applied.

In Step S42, a one-dimensional maximum value filter having a pixel width of (2 m+1) is applied (n−m+1) times to the one-dimensional minimum value filtered projection profile $P_{min}$. Specifically, when the projection value of an i-th channel in the projection profile $P_{min}$ is represented as $P_{min}(i)$, a process in which the maximum value of $P_{min}(i-m)$—$P_{min}(i+m)$ is set in $P_{min}(i)$ is repeated (n−m+1) times, wherein m=1 and n=1, for example. A projection profile $P_{max}$ after the one-dimensional maximum value filter is applied is exemplarily shown in FIG. 8. As can be seen from FIG. 8, the profile of the top plate has been removed. Then, the one-dimensional maximum value filtered projection profile $P_{max}$ is passed to Step S5 instead of the projection profile of the 90° parallel view.

Many widely different embodiments of the invention may be configured without departing from the spirit and the scope of the present invention. It should be understood that the present invention is not limited to the specific embodiments described in the specification, except as defined in the appended claims.

What is claimed is:

1. A subject center position detection method comprising the steps of:

acquiring a projection profile by imaging a subject from a direction orthogonal to a plane containing a body axis of the subject by an X-ray CT apparatus for performing a scan by an X-ray tube rotating around the subject;

defining an X-ray detector channel index corresponding to a calculated centroid of said projection profile as a centroid channel index;

examining a projection value in said projection profile toward a direction along a first direction of the subject from said centroid channel index;

defining a channel index having a projection value no more than a predetermined projection value threshold $P_{th}$ as a first threshold channel index;

examining on the other hand a projection value in said projection profile toward a direction along a second direction of the subject opposite to said first direction from said centroid channel index;

defining a channel index having a projection value no more than the predetermined projection value threshold $P_{th}$ as a second threshold channel index;

defining an intermediate value between said first and second threshold channel indices as a subject position channel index; and obtaining a subject center position from said subject position channel index.

2. The subject center position detection method as defined by claim 1, wherein said projection value threshold $P_{th}$ is ½ of a projection value corresponding to said centroid channel index.

3. The subject center position detection method as defined by claim 1, further comprising the steps of: removing profiles other than the subject's profile from said projection profile, and then calculating said centroid.

4. An X-ray CT imaging method for performing a scan by an X-ray tube rotating around a subject, said method comprising the steps of:

acquiring a projection profile of a parallel view of a view angle of 90° by imaging said subject;

detecting a center position of said subject based on said projection profile;

providing a predetermined range of distances between said center position and a scan center;

calculating a calculated distance between said center position and said scan center; and providing a warning signal when said calculated distance exceeds said predetermined range so that distance between said center position and said scan center can be adjusted to be within said predetermined range.

5. An X-ray CT apparatus for performing a scan by an X-ray tube rotating around a subject, comprising subject center position detection means configured to:

define an X-ray detector channel index corresponding to a calculated centroid of a projection profile acquired by imaging a subject from a direction orthogonal to a plane containing a body axis of the subject as a centroid channel index;

examine a projection value in said projection profile toward a direction along a first direction of the subject from said centroid channel index;

define a channel index having a projection value no more than a predetermined projection value threshold $P_{th}$ as a first threshold channel index;

examine on the other hand a projection value in said projection profile toward a direction along a second direction of the subject opposite to said first direction from said centroid channel index;

define a channel index having a projection value no more than the predetermined projection value threshold $P_{th}$ as a second threshold channel index;

define an intermediate value between said first and second threshold channel indices as a subject position channel index; and obtain a subject center position from said subject position channel index.

6. The X-ray CT apparatus as defined by claim 5, wherein said projection value threshold $P_{th}$ is ½ of a projection value corresponding to said centroid channel index.

7. The X-ray CT apparatus as defined by claim 5, further configured to remove profiles other than the subject's profile from said projection profile, and then calculate said centroid.

8. An X-ray CT apparatus for performing a scan by an X-ray tube rotating around a subject, said apparatus comprising:

first means for acquiring a projection profile of a parallel view of a view angle of 90° by imaging said subject;

second means for detecting a center position of said subject based on said projection profile;

third means for providing a predetermined range of distances between said center position and said scan center;

fourth means for calculating a calculated distance between said center position and said scan center; and fifth means for displaying a warning when said calculated distance exceeds said predetermined range so that distance between said center position and said scan center can be adjusted to be within said predetermined range.

* * * * *